(12) United States Patent
Griffin et al.

(10) Patent No.: US 10,207,077 B2
(45) Date of Patent: *Feb. 19, 2019

(54) MEDICAL DEVICE

(71) Applicant: BOSTON SCIENTIFIC SCIMED, INC., Maple Grove, MN (US)

(72) Inventors: Stephen Griffin, San Jose, CA (US); Elaine Lim, Fremont, CA (US); Gregory E. Mirigian, Dublin, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/455,708

(22) Filed: Mar. 10, 2017

(65) Prior Publication Data

US 2017/0182291 A1 Jun. 29, 2017

Related U.S. Application Data

(63) Continuation of application No. 14/687,685, filed on Apr. 15, 2015, now Pat. No. 9,592,363, which is a
(Continued)

(51) Int. Cl.
*A61M 25/00* (2006.01)
*A61M 25/01* (2006.01)
*A61L 29/02* (2006.01)

(52) U.S. Cl.
CPC ...... *A61M 25/0054* (2013.01); *A61M 25/001* (2013.01); *A61M 25/0045* (2013.01);
(Continued)

(58) Field of Classification Search
CPC .......... A61M 25/0054; A61M 25/0097; A61M 25/0068; A61M 25/0108; A61M 25/0051;
(Continued)

(56) References Cited

U.S. PATENT DOCUMENTS

| 1,553,227 A | 9/1925 | Feyk et al. |
| 1,866,888 A | 7/1932 | Hawley |

(Continued)

FOREIGN PATENT DOCUMENTS

| AU | 723040 B2 | 8/2000 |
| AU | 733966 B2 | 5/2001 |

(Continued)

*Primary Examiner* — Theodore Stigell
(74) *Attorney, Agent, or Firm* — Seager, Tufte & Wickhem, LLP

(57) ABSTRACT

A medical device including a shaft having an elongated inner member and an elongated tubular reinforcing member disposed over at least a portion of the inner member. In some embodiments, at least a portion of the outer surface of the inner member is spaced from the inner surface of the reinforcing member, defining a space substantially free of any other structures of the device. In some embodiments, the shaft can include a tip structure disposed on a distal portion of the inner member. In some such embodiments, the reinforcing member has a distal end, and the tip structure is disposed on the distal portion of the inner member adjacent the distal end of the reinforcing member. Additionally, in some embodiments, the reinforcing member can include a plurality of apertures defined therein, for example, to enhance the flexibility or other such characteristics of all or portions of the reinforcing member.

18 Claims, 5 Drawing Sheets

Related U.S. Application Data continuation of application No. 14/166,504, filed on Jan. 28, 2014, now Pat. No. 9,023,011, which is a continuation of application No. 13/477,755, filed on May 22, 2012, now Pat. No. 8,636,716, which is a continuation of application No. 12/470,261, filed on May 21, 2009, now Pat. No. 8,182,465, which is a continuation of application No. 11/180,187, filed on Jul. 13, 2005, now Pat. No. 7,540,865, which is a continuation of application No. 10/400,750, filed on Mar. 27, 2003, now Pat. No. 7,001,369.

(52) U.S. Cl.
CPC .... *A61M 25/0051* (2013.01); *A61M 25/0053* (2013.01); *A61M 25/0068* (2013.01); *A61M 25/0097* (2013.01); *A61M 25/0108* (2013.01); *A61L 29/02* (2013.01); *A61M 2025/0046* (2013.01); *A61M 2205/0216* (2013.01); *A61M 2205/0227* (2013.01); *A61M 2205/0266* (2013.01)

(58) Field of Classification Search
CPC .......... A61M 25/0053; A61M 25/0045; A61M 25/001; A61M 2205/0216; A61M 2025/0046; A61M 2205/0266; A61M 2205/0227
See application file for complete search history.

(56) References Cited

U.S. PATENT DOCUMENTS

| | | |
|---|---|---|
| 2,275,827 A | 3/1942 | Plensler |
| 2,413,805 A | 1/1947 | Vickers |
| 2,441,166 A | 5/1948 | Raspet |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,523 A | 8/1967 | Rieser |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,318,402 A | 3/1982 | Vaillancourt |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,547,192 A | 10/1985 | Brodsky et al. |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa et al. |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | de Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Towne et al. |
| 5,063,935 A | 11/1991 | Gambale |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,195,984 A | 3/1993 | Schatz |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |

(56) References Cited

U.S. PATENT DOCUMENTS

| | | |
|---|---|---|
| 5,341,818 A | 8/1994 | Abrams et al. |
| 5,345,937 A | 9/1994 | Middleman et al. |
| 5,345,945 A | 9/1994 | Hodgson et al. |
| 5,358,493 A | 10/1994 | Schweich, Jr. et al. |
| 5,365,942 A | 11/1994 | Shank |
| 5,365,943 A | 11/1994 | Jansen |
| 5,368,564 A | 11/1994 | Savage |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams et al. |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,460,960 A | 10/1995 | Kim et al. |
| 5,470,330 A | 11/1995 | Goldenberg et al. |
| 5,476,701 A | 12/1995 | Berger |
| 5,477,856 A | 12/1995 | Lundquist |
| 5,480,382 A | 1/1996 | Hammerslag et al. |
| 5,496,294 A * | 3/1996 | Hergenrother .... A61M 25/0052 604/264 |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A * | 11/1996 | Schwartz .......... A61M 25/0013 604/264 |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |
| 5,641,818 A | 6/1997 | Sweet |
| 5,656,011 A | 8/1997 | Uihlein et al. |
| 5,658,264 A | 8/1997 | Samson |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,702,373 A | 12/1997 | Samson |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Harrigan et al. |
| 5,797,856 A | 8/1998 | Frisbie et al. |
| 5,800,408 A * | 9/1998 | Strauss ............... A61M 25/007 137/625.47 |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,923 A | 11/1998 | Mayer |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Berenstein et al. |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone et al. |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A * | 3/2000 | Solar ..................... A61M 25/09 600/585 |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |

(56) References Cited

U.S. PATENT DOCUMENTS

| | | | |
|---|---|---|---|
| 6,375,774 B1 | 4/2002 | Lunn et al. | |
| 6,379,369 B1 | 4/2002 | Abrams et al. | |
| 6,390,993 B1 | 5/2002 | Cornish et al. | |
| 6,398,758 B1 | 6/2002 | Jacobsen et al. | |
| 6,428,489 B1 | 8/2002 | Jacobsen et al. | |
| 6,428,512 B1 | 8/2002 | Anderson et al. | |
| 6,431,039 B1 | 8/2002 | Jacobsen et al. | |
| 6,440,088 B1 | 8/2002 | Jacobsen et al. | |
| 6,478,778 B1 | 11/2002 | Jacobsen et al. | |
| 6,488,637 B1 | 12/2002 | Eder et al. | |
| 6,491,648 B1 | 12/2002 | Cornish et al. | |
| 6,491,671 B1 | 12/2002 | Larson, III et al. | |
| 6,503,244 B2 | 1/2003 | Hayman | |
| 6,508,803 B1 | 1/2003 | Horikawa et al. | |
| 6,524,301 B1 | 2/2003 | Wilson et al. | |
| 6,530,934 B1 | 3/2003 | Jacobsen et al. | |
| 6,547,779 B2 | 4/2003 | Levine et al. | |
| 6,553,880 B2 | 4/2003 | Jacobsen et al. | |
| 6,556,873 B1 | 4/2003 | Smits | |
| 6,579,246 B2 | 6/2003 | Jacobsen et al. | |
| 6,602,280 B2 | 8/2003 | Chobotov | |
| 6,610,046 B1 | 8/2003 | Usami et al. | |
| 6,623,448 B2 | 9/2003 | Slater | |
| 6,636,758 B2 | 10/2003 | Sanchez et al. | |
| 6,638,266 B2 | 10/2003 | Wilson et al. | |
| 6,652,508 B2 | 11/2003 | Griffin et al. | |
| 6,682,493 B2 | 1/2004 | Mirigian | |
| 6,712,826 B2 | 3/2004 | Lui | |
| 6,730,095 B2 | 5/2004 | Olson, Jr. et al. | |
| 6,749,560 B1 | 6/2004 | Konstorum et al. | |
| 6,766,720 B1 | 7/2004 | Jacobsen et al. | |
| 6,777,644 B2 | 8/2004 | Peacock, III et al. | |
| 6,811,544 B2 | 11/2004 | Schaer | |
| 6,837,898 B2 | 1/2005 | Boyle et al. | |
| 6,866,642 B2 | 3/2005 | Kellerman et al. | |
| 6,887,235 B2 | 5/2005 | O'Connor et al. | |
| 6,918,882 B2 | 7/2005 | Skujins et al. | |
| 6,997,937 B2 | 2/2006 | Jacobsen et al. | |
| 7,001,369 B2 * | 2/2006 | Griffin | A61M 25/0051 604/264 |
| 7,074,197 B2 | 7/2006 | Reynolds et al. | |
| 7,540,865 B2 * | 6/2009 | Griffin | A61M 25/0051 604/264 |
| 7,914,466 B2 | 3/2011 | Davis et al. | |
| 7,955,272 B2 | 6/2011 | Rooney et al. | |
| 8,048,004 B2 | 11/2011 | Davis et al. | |
| 8,048,060 B2 * | 11/2011 | Griffin | A61M 25/0051 604/264 |
| 8,182,465 B2 * | 5/2012 | Griffin | A61M 25/0051 604/264 |
| 8,636,716 B2 * | 1/2014 | Griffin | A61M 25/0051 604/264 |
| 9,023,011 B2 * | 5/2015 | Griffin | A61M 25/0051 604/524 |
| 9,592,363 B2 * | 3/2017 | Griffin | A61M 25/0051 |
| 2002/0013540 A1 | 1/2002 | Jacobsen et al. | |
| 2002/0019599 A1 | 2/2002 | Rooney et al. | |
| 2003/0009208 A1 | 1/2003 | Snyder et al. | |
| 2003/0060732 A1 | 3/2003 | Jacobsen et al. | |
| 2003/0069520 A1 | 4/2003 | Skujins et al. | |
| 2003/0069521 A1 | 4/2003 | Reynolds et al. | |
| 2003/0069522 A1 | 4/2003 | Jacobsen et al. | |
| 2004/0097880 A1 * | 5/2004 | Schur | A61M 25/007 604/164.01 |
| 2004/0167437 A1 | 8/2004 | Sharrow et al. | |
| 2004/0181174 A2 | 9/2004 | Davis et al. | |
| 2004/0181176 A1 | 9/2004 | Jafari et al. | |
| 2006/0189896 A1 | 8/2006 | Davis et al. | |
| 2006/0264904 A1 | 11/2006 | Kerby et al. | |
| 2008/0021347 A1 | 1/2008 | Jacobsen et al. | |
| 2008/0021348 A1 | 1/2008 | Jacobsen et al. | |
| 2008/0021400 A1 | 1/2008 | Jacobsen et al. | |
| 2008/0021401 A1 | 1/2008 | Jacobsen et al. | |
| 2008/0021402 A1 | 1/2008 | Jacobsen et al. | |
| 2008/0021403 A1 | 1/2008 | Jacobsen et al. | |
| 2008/0021404 A1 | 1/2008 | Jacobsen et al. | |
| 2008/0021405 A1 | 1/2008 | Jacobsen et al. | |
| 2008/0021406 A1 | 1/2008 | Jacobsen et al. | |
| 2008/0021407 A1 | 1/2008 | Jacobsen et al. | |
| 2008/0021408 A1 | 1/2008 | Jacobsen et al. | |
| 2008/0077119 A1 | 3/2008 | Snyder et al. | |

FOREIGN PATENT DOCUMENTS

| | | |
|---|---|---|
| BR | 9712829 A | 1/2000 |
| CA | 2255781 A1 | 11/1997 |
| CA | 2266685 C | 5/2006 |
| CN | 1230914 A | 10/1999 |
| DE | 2539191 A1 | 3/1976 |
| DE | 3621967 A1 | 1/1988 |
| EP | 0045931 A2 | 2/1982 |
| EP | 0069522 A1 | 1/1983 |
| EP | 0087933 A1 | 9/1983 |
| EP | 0111044 A2 | 6/1984 |
| EP | 0181174 A2 | 5/1986 |
| EP | 0377453 A1 | 7/1990 |
| EP | 0521595 A2 | 1/1993 |
| EP | 0565065 A1 | 10/1993 |
| EP | 0608853 A2 | 8/1994 |
| EP | 0778038 A2 | 6/1997 |
| EP | 0778039 A1 | 6/1997 |
| EP | 0778040 A2 | 6/1997 |
| EP | 0790066 A2 | 8/1997 |
| EP | 0812599 A2 | 12/1997 |
| EP | 0865772 A1 | 9/1998 |
| EP | 0865773 A1 | 9/1998 |
| EP | 0917885 A1 | 5/1999 |
| EP | 0937481 A1 | 8/1999 |
| EP | 0935947 B1 | 12/2004 |
| EP | 0934141 B1 | 11/2005 |
| GB | 2214354 A | 8/1989 |
| GB | 2257269 A | 1/1993 |
| JP | 588522 | 1/1983 |
| JP | 60091858 A | 5/1985 |
| JP | 61022752 A | 1/1986 |
| JP | 62023361 A | 1/1987 |
| JP | 62089470 A | 4/1987 |
| JP | 62299277 A | 12/1987 |
| JP | 63093516 A | 4/1988 |
| JP | 63181774 A | 7/1988 |
| JP | 63217966 A | 9/1988 |
| JP | 1089956 A | 4/1989 |
| JP | 1135363 A | 5/1989 |
| JP | 1158936 A | 6/1989 |
| JP | 2107268 A | 4/1990 |
| JP | 3081831 A | 4/1991 |
| JP | 03122850 A | 12/1991 |
| JP | 4061840 A | 2/1992 |
| JP | 4099963 A | 3/1992 |
| JP | 4213069 A | 8/1992 |
| JP | 4213070 A | 8/1992 |
| JP | 4236965 A | 8/1992 |
| JP | 5149969 A | 6/1993 |
| JP | 5506806 T | 10/1993 |
| JP | 5309519 A | 11/1993 |
| JP | 5507857 T | 11/1993 |
| JP | 6169996 A | 6/1994 |
| JP | 6277296 A | 10/1994 |
| JP | 6312313 A | 11/1994 |
| JP | 728562 U | 5/1995 |
| JP | 7124164 A | 5/1995 |
| JP | 7124263 A | 5/1995 |
| JP | 7136280 A | 5/1995 |
| JP | 7418264 A | 6/1995 |
| JP | 7185009 A | 7/1995 |
| JP | 7255855 A | 10/1995 |
| JP | 7275366 A | 10/1995 |
| JP | 751067 A | 11/1995 |
| JP | 8229888 A | 9/1996 |
| JP | 8317988 A | 12/1996 |
| JP | 9010315 A | 1/1997 |
| JP | 9000164 A | 4/1997 |
| JP | 9192235 A | 7/1997 |

(56) References Cited

FOREIGN PATENT DOCUMENTS

| | | | |
|---|---|---|---|
| JP | 9253214 | A | 9/1997 |
| JP | 9276413 | A | 10/1997 |
| JP | 9294813 | A | 11/1997 |
| JP | 10057501 | A | 3/1998 |
| JP | 10118193 | A | 5/1998 |
| JP | 10305039 | A | 11/1998 |
| JP | 11267224 | A | 10/1999 |
| JP | 11342196 | A | 12/1999 |
| JP | 2000197704 | A | 7/2000 |
| JP | 2000510722 | A | 8/2000 |
| JP | 2000511083 | A | 8/2000 |
| JP | 2001500808 | A | 1/2001 |
| JP | 2002529137 | A | 9/2002 |
| JP | 2002542901 | A | 12/2002 |
| JP | 2002543896 | A | 12/2002 |
| JP | 2003517893 | A | 6/2003 |
| JP | 3649604 | B2 | 2/2005 |
| JP | 2005534407 | A | 11/2005 |
| SU | 712908 | A1 | 1/1980 |
| SU | 758421 | A1 | 8/1980 |
| SU | 7529365 | A1 | 12/1989 |
| WO | 9002520 | A1 | 3/1990 |
| WO | 9113364 | A1 | 9/1991 |
| WO | 9204072 | A1 | 3/1992 |
| WO | 9207619 | A1 | 5/1992 |
| WO | 9304722 | A2 | 3/1993 |
| WO | 9311313 | A1 | 6/1993 |
| WO | 9524263 | A1 | 9/1995 |
| WO | 9619255 | A1 | 6/1996 |
| WO | 9710022 | A2 | 3/1997 |
| WO | 9725914 | A1 | 7/1997 |
| WO | 9743949 | A1 | 11/1997 |
| WO | 9744083 | A1 | 11/1997 |
| WO | 9744086 | A1 | 11/1997 |
| WO | 9810694 | A2 | 3/1998 |
| WO | 9904847 | A1 | 2/1999 |
| WO | 9911313 | A1 | 3/1999 |
| WO | 0027303 | A2 | 5/2000 |
| WO | 0030710 | A1 | 6/2000 |
| WO | 0048645 | A2 | 8/2000 |
| WO | 0057943 | A1 | 10/2000 |
| WO | 0066199 | A1 | 11/2000 |
| WO | 0067845 | A1 | 11/2000 |
| WO | 0072907 | A1 | 12/2000 |
| WO | 0128620 | A1 | 4/2001 |
| WO | 0136034 | A2 | 5/2001 |
| WO | 0145773 | A1 | 6/2001 |
| WO | 0145912 | A1 | 6/2001 |
| WO | 0193920 | A2 | 12/2001 |
| WO | 0213682 | A1 | 2/2002 |
| WO | 02062540 | A2 | 8/2002 |
| WO | 03004086 | A2 | 1/2003 |
| WO | 03008148 | A2 | 1/2003 |
| WO | 2004012804 | A2 | 2/2004 |
| WO | 2004047899 | A2 | 2/2004 |

\* cited by examiner

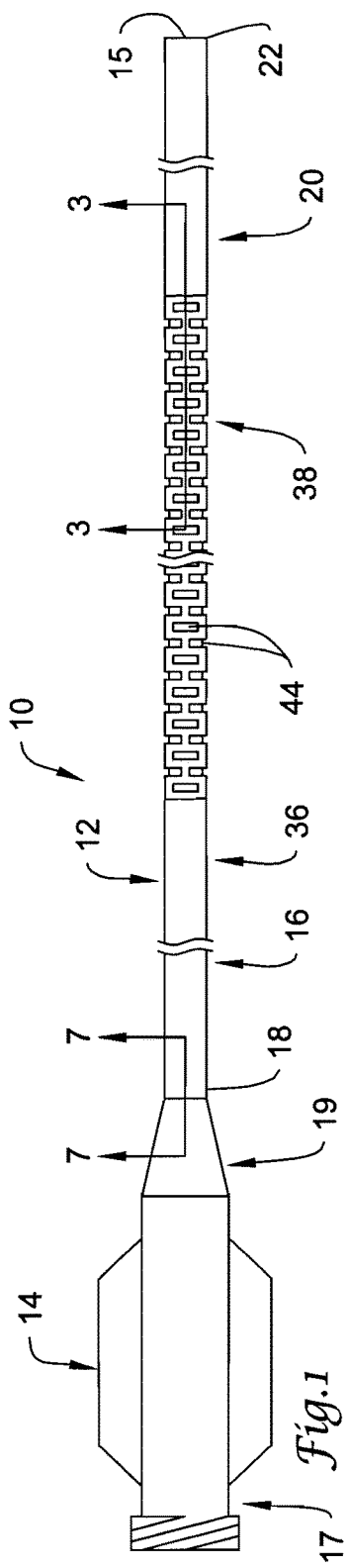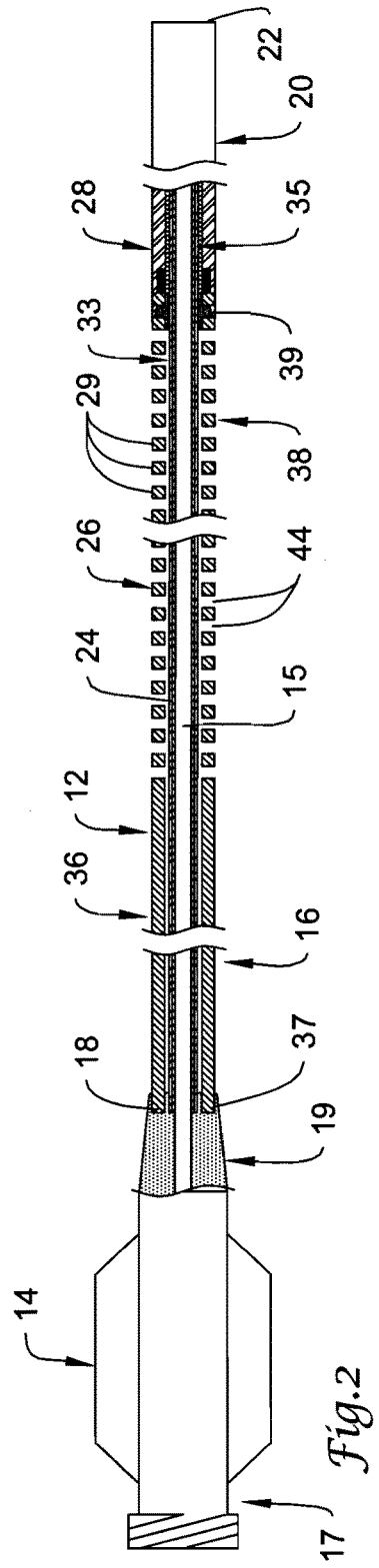

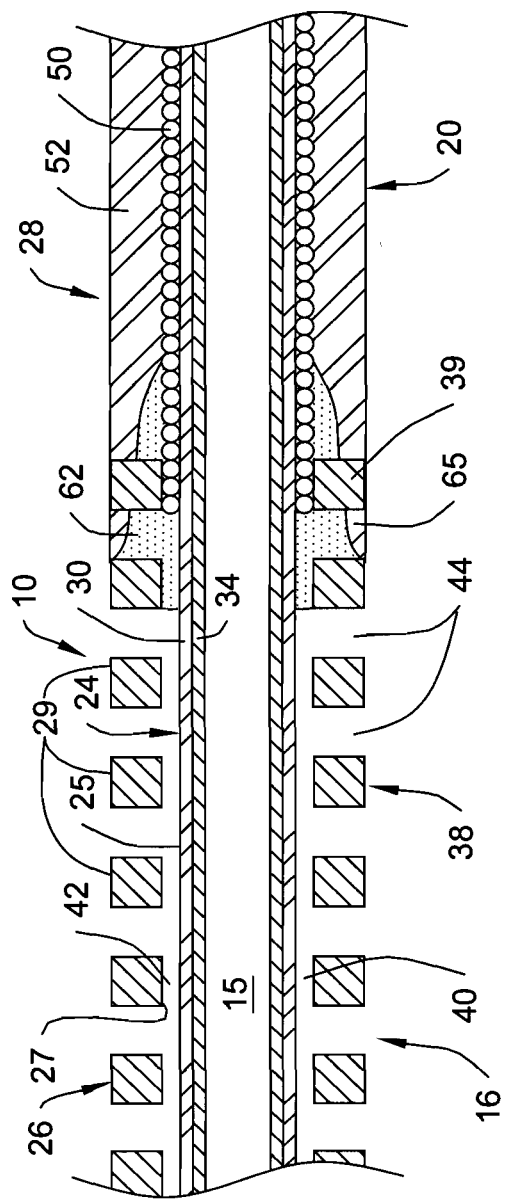

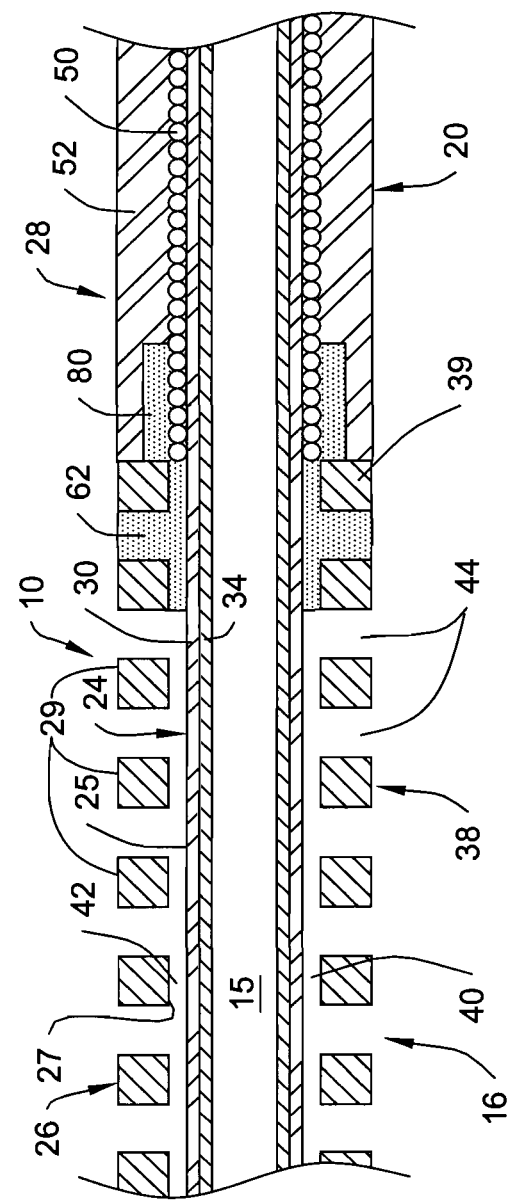

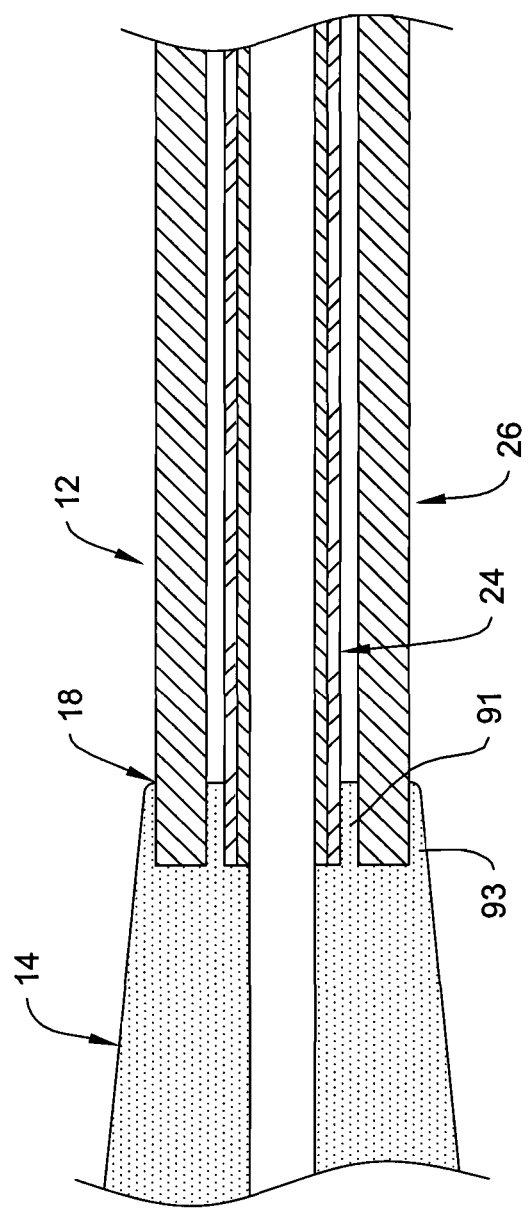

MEDICAL DEVICE

CROSS REFERENCE TO RELATED APPLICATIONS

This application is a continuation of U.S. application Ser. No. 14/687,685, filed Apr. 15, 2015, now U.S. Pat. No. 9,592,363; which is a continuation of U.S. application Ser. No. 14/166,504, filed Jan. 28, 2014, now U.S. Pat. No. 9,023,011; which is a continuation of U.S. application Ser. No. 13/477,755, filed May 22, 2012, now U.S. Pat. No. 8,636,716; which is a continuation of U.S. application Ser. No. 12/470,261, filed May 21, 2009, now U.S. Pat. No. 8,182,465; which is a continuation of U.S. application Ser. No. 11/180,187, filed Jul. 13, 2005, now U.S. Pat. No. 7,540,865; which is a continuation of U.S. application Ser. No. 10/400,750, filed Mar. 27, 2003, now U.S. Pat. No. 7,001,369, the disclosures of which are incorporated herein by reference.

This application is also related to U.S. application Ser. No. 11/505,119, filed Aug. 16, 2006, now U.S. Pat. No. 8,048,060, the disclosure of which is incorporated herein by reference.

FIELD OF THE INVENTION

The invention relates generally to medical devices. More specifically, the invention relates to a medical device, such as a catheter or the like, including an elongated shaft having a reinforcing member disposed about a portion of the shaft.

BACKGROUND

A wide variety of medical devices have been developed for intracorporal use. Elongated medical devices are commonly used to facilitate navigation through and/or treatment within the anatomy of a patient. A variety of elongate medical devices such as catheters, endoscopes and the like have been developed over the past several decades. Because the anatomy of a patient may be very tortuous, it is desirable to combine a number of performance features in such devices. For example, it is sometimes desirable that the device have a relatively high level of pushability and torqueability, particularly near its proximal end. It is also sometimes desirable that a device be relatively flexible, particularly near its distal end. A number of different elongated medical device structures and assemblies are known, each having certain advantages and disadvantages. However, there is an ongoing need to provide alternative elongated medical device structures and assemblies.

SUMMARY OF SOME EMBODIMENTS

The invention provides design, material, and manufacturing method alternatives for medical devices. In some embodiments, the medical devices can include a shaft having an elongated inner tubular member and an elongated tubular reinforcing member disposed over a portion of the inner tubular member. In some embodiments, the reinforcing member is disposed about a proximal portion of the inner tubular member such that a distal portion of the inner tubular member is free of the reinforcing member. In some embodiments, at least a portion of an outer surface of the inner tubular member is spaced from an inner surface of the reinforcing member. In some embodiments, the shaft can include a tip structure disposed on the distal portion of the inner tubular member. In some such embodiments, reinforcing member has a distal end, and the tip structure is disposed on the distal portion of the inner tubular member adjacent the distal end of the reinforcing member. Additionally, in some embodiments, the reinforcing member can include a plurality of apertures defined therein, for example, to enhance the flexibility or other such characteristics of all or portions of the reinforcing member.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a partial side plan view of a medical device in accordance with one example embodiment of the invention, shown as a guide or diagnostic catheter;

FIG. 2 a partial cross sectional view of a portion of the medical device of FIG. 1;

FIG. 5 is a partial cross sectional view similar to the view of FIG. 3, but of another example embodiment of a medical device;

FIG. 6 is a partial cross sectional view similar to the view of FIG. 3, but of another example embodiment of a medical device; and FIG. 7 is a cross sectional view taken along line 7-7 of FIG. 1.

Figure 3:
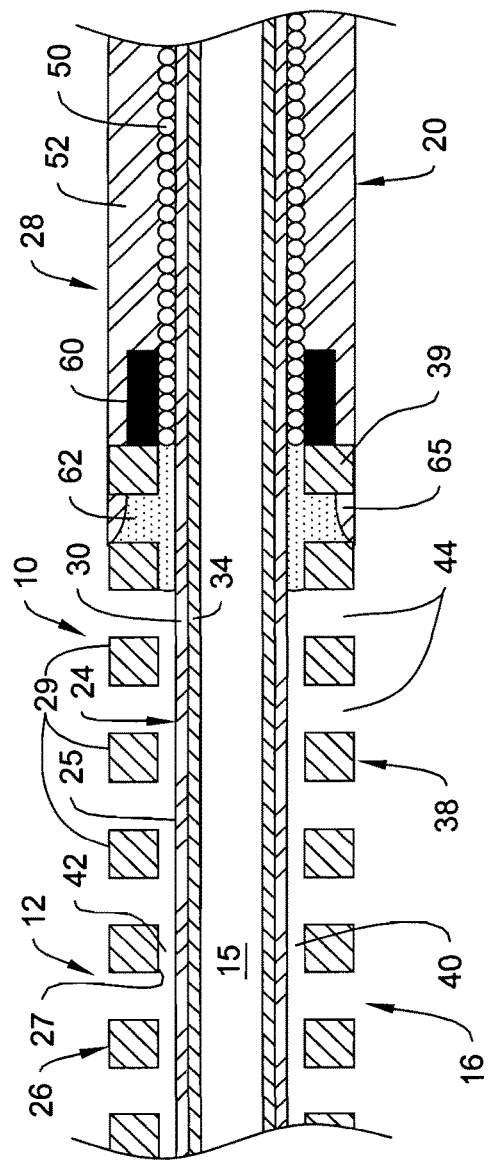
FIG. 3 is a partial cross sectional view of a portion of the medical device of FIG. 1, taken along line 3-3 of FIG. 1.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS OF THE INVENTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Refer now to FIG. 1 which illustrates a medical device 10 in accordance with one example embodiment. In the embodiment shown, the medical device 10 is in the form of a guide or diagnostic catheter. Although set forth with specific reference to a guide or diagnostic catheter in the example embodiments shown in the Figures and discussed below, the invention may relate to virtually any medical device including an elongate shaft or member having a reinforcing member disposed thereon. For example, the invention may be applied to medical devices such as a balloon catheter, an atherectomy catheter, a drug delivery catheter, a stent delivery catheter, an endoscope, an introducer sheath (if the sheath includes a reinforcing member), a fluid delivery device, other infusion or aspiration devices, device delivery (i.e. implantation) devices, and the like. Thus, while the Figures and descriptions below are directed toward a guide or diagnostic catheter, in other applications sizes in terms of diameter and length may vary widely, depending upon the desired properties of a particular device. For example, in some devices, lengths may range from about 1-300 centimeters or more, while outside diameters may range from about 1 F to about 20 F, or even more in some embodiments.

As shown in FIG. 1, the catheter 10 can include an elongate shaft 12 including a proximal portion 16 having a proximal end 18, and distal portion 20 having a distal end 22. The shaft 12 is a generally tubular member defining a lumen 15 therein. A manifold 14 can be connected to the proximal end of the elongate shaft 12, and include a lumen and/or other structure to facilitate connection to other medical devices (e.g., syringe, Y-adapter, etc.) and to provide access to lumen 15 within the shaft 12. The manifold may include a hub portion 17 and a strain relief portion 19. In some embodiments, the shaft 12 may include additional devices or structures such as inflation or anchoring members, sensors, optical elements, ablation devices or the like, depending upon the desired function and characteristics of the catheter 10.

The guide or diagnostic catheter 10 may have a length and an outside diameter appropriate for its desired use, for example, to enable intravascular insertion and navigation. For example, the catheter 10 may have a length of about 20 cm-250 cm and an outside diameter of approximately 1 F-10 F, when catheter 10 is adapted as a guide catheter. In some embodiments, the catheter 10 can be a microcatheter that is adapted and/or configured for use within small anatomies of the patient. For example, some embodiments are particularly useful in treating targets located in tortuous and narrow vessels, for example in the neurovascular system, or in certain sites within the coronary vascular system, or in sites within the peripheral vascular system such as superficial femoral, popliteal, or renal arteries. The target site in some embodiments is a neurovascular site, such as site in the brain, which is accessible only via a tortuous vascular path, for example, a vascular path containing a plurality of bends or turns which may be greater than 90° turns, and/or involving vessels which are in the range of about 8 mm or less, and in some cases as small as 2-3 mm or less, in diameter. However, it is contemplated that the catheter may be used in other target sites within the anatomy of a patient. In some embodiments, the catheter can include an outside diameter in the range of approximately 1 F-4 F.

While in some embodiments, the catheter 10 can be described in terms of intravascular use, in other embodiments the guide or diagnostic catheter 10 may be suited for other uses in the digestive system, soft tissues, or any other use including insertion into an organism for medical uses. For example, in some embodiments, the catheter 10 may be significantly shorter and used as an introducer sheath, for example, while in other embodiments the catheter 10 may be adapted for other medical procedures. The guide or diagnostic catheter 10 may also include additional structure and materials that are substantially conventional.

Additionally, although depicted as including a generally round cross-sectional shape, it can be appreciated that the shaft 12 can include other cross-sectional shapes or combinations of shapes without departing from the spirit of the invention. For example, the cross-sectional shape of the generally tubular shaft 12 may be oval, rectangular, square, triangular, polygonal, and the like, or any other suitable shape, depending upon the desired characteristics.

Refer now to FIG. 2, which shows a partial cross sectional view of the shaft 12 including the proximal portion 16, the distal portion 20, and the manifold 14 connected to the proximal end 18. The shaft 12 can include an inner tubular member 24 defining the lumen 15. The shaft 12 can also include a reinforcing member 26 disposed about a portion of the inner tubular member 24, and a distal tip structure 28 disposed about a distal portion of the inner tubular member 24. Some example structures and components for use in each of these structures will now be discussed in greater detail.

The inner tubular member 24 can extend from a point within the distal portion 20 to a point within the proximal portion 16 of the shaft 12. The length of the inner tubular member 24 can vary, depending upon, for example, the length of the shaft 12, the desired characteristics and functions of the catheter 10, and other such parameters. In some embodiments, the inner tubular member 24 can extend substantially the entire length of the shaft 12, for example, from a point adjacent the proximal end 18 to a point adjacent the distal end 22. For example, the length of the inner tubular member 24 can be in the range of about 1-300 centimeters or more, or in some embodiments in the range of about 20 cm-250 cm. In some embodiments, the inner tubular member 24 can include a proximal portion 33 and a distal portion 35, which can be any proximal or distal sections of the inner tubular member 24, but in some cases can be defined with regard to the placement of the reinforcing member 26 along the length of the inner tubular member. For example, in some embodiments, the distal portion 35 can be any portion of the inner tubular member 24 that is distal of the reinforcing member 26, while the proximal portion 35 can be any portion of the inner tubular member 24 that is disposed within, or is proximal of a distal end 39 of reinforcing member 26. In some embodiments, the distal portion 35 can have a length in the range of 1 cm or greater, or in the range of about 2 cm or greater, and in some embodiments in the range of about 3 to about 20 cm.

As indicated above, the inner tubular member 24 defines a lumen 15. The lumen 15 can be adapted and/or configured to facilitate, for example, insertion of other medical devices (e.g., guide wires, balloon catheters, etc.) there through, and/or to facilitate injection of fluids (e.g., radiopaque dye, saline, drugs, inflation fluid, etc.) there through. The size of the lumen can vary, depending upon the desired characteristics and intended use. In some embodiments, the inner tubular member 24 can have an inner diameter, defining the lumen 15, that is in the range of about 0.01 to about 0.05 inch in size, and in some embodiments, in the range of about 0.015 to about 0.03 inch in size, and in some embodiments, in the range of about 0.016 to about 0.026 inch in size. Additionally, in some embodiments, the inner tubular member 24 can have an outer diameter that is in the range of about 0.011 to about 0.055 inch in size, and in some embodiments, in the range of about 0.015 to about 0.03 inch in size, and in some embodiments, in the range of about 0.019 to about 0.029 inch in size. It should be understood however, that these dimensions are provided by way of example embodiments only, and that in other embodiments, the size of the inner and outer diameter of the inner tubular member 24 can vary greatly from the dimensions given, depending upon the desired characteristics and function of the device. In some embodiments, the inner tubular member 24, or other portions of the shaft 12, can define one or more additional lumens depending upon the desired characteristics and function of the catheter 10, and such additional lumens can be shaped, size, adapted and/or configured the same as or different from lumen 15, depending upon the desired characteristic and functions.

The inner tubular member 24 may be one or more layers. As best seen in FIG. 3, the inner tubular member 24 may be multi-layered. In the illustrative embodiment, the inner tubular member 24 may include an outer layer 30, and an inner layer 34. It should be understood that more or fewer layers can be used depending upon the desired characteristics of the device. Furthermore, while an outer layer 30 and inner layer 34 are described with respect to the particular embodiment, these layers 30, 34 may be provided as a single layer. For example, the inner layer 34 and outer layer 30 may be provided separately, but attached or combined together to physically form a single layer.

Inner layer 34 and outer layer 30 may be made of any suitable material and by any suitable process, the materials and processes varying with the particular application. Examples of some suitable materials include, but are not limited to, polymers, metals, metal alloys, or composites or combinations thereof. Some examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, etc., or mixtures, blends or combinations thereof, and may also include or be made up of a lubricous polymer. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The inner layer 34 may include a lubricious polymer such as HDPE or PTFE, for example, or a copolymer of tetrafluoroethylene with perfluoroalkyl vinyl ether (PFA) (more specifically, perfluoropropyl vinyl ether or perfluoromethyl vinyl ether), or the like. The outer layer 30 may include a flexible polymer such as polyether block amide or polyether-ester elastomer. Additionally, in some embodiments, the polymer material of the inner layer 34 and/or outer layer 30 can be blended with a liquid crystal polymer (LCP). For example, in some embodiments, the mixture can contain up to about 5% LCP. This has been found in some embodiments to enhance torqueability.

Additionally, as suggested above, in some embodiments, the inner tubular member 24 may include or be made of metal or metal alloys. Some examples of suitable metals and metal alloys can include stainless steel, such as 304V, 304L, and 316L stainless steel; nickel-titanium alloy such as a superelastic (i.e. pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it is desirable to use metals, or metal alloys that are suitable for metal joining techniques such as welding, soldering, brazing, crimping, friction fitting, adhesive bonding, etc.

The inner tubular member 24 can be formed by any suitable method or technique. For example in some embodiments, the inner layer 34 can be formed separately, and thereafter the outer layer 30 can be disposed thereon by suitable techniques, such as extrusion, co-extrusion, interrupted layer co-extrusion (ILC), coating, heat shrink techniques, casting, molding, or by fusing one or several segments of an outer layer material end-to-end about the inner layer 34, or the like. In some other embodiments, the layers 30/34 may be formed together using suitable techniques, such as extrusion, co-extrusion, interrupted layer co-extrusion (ILC), heat shrink techniques, fusing, or the like. In yet other embodiments, the layers 30/34 can be formed separately, such as by extrusion, co-extrusion, interrupted layer co-extrusion (ILC), casting, molding, heat shrink techniques, fusing, or the like, and thereafter coupled or connected together using suitable techniques, such as heat shrink techniques, friction fitting, mechanically fitting, chemically bonding, thermally bonding, welding (e.g., resistance, Rf, or laser welding), soldering, brazing, adhesive bonding, crimping, or the use of a connector member or material, or the like, or combinations thereof.

The inner tubular member 24 may have a uniform stiffness, or may vary in stiffness along its length. For example, a gradual reduction in stiffness from the proximal end to the distal end thereof may be achieved, depending upon the desired characteristics. The gradual reduction in stiffness may be continuous or may be stepped, and may be achieved, for example, by varying the structure, such as the size or thickness of one or more of the layers 30/34, or for example, by varying the materials used in one or more of the layers 30/34. Such variability in characteristics and materials can be achieved, for example, by using techniques such as ILC, or by fusing together separate extruded tubular segments. Additionally, the inner and/or the outer layer, 34/30 or both, may be impregnated with, or be made of or include a radiopaque material to facilitate radiographic visualization. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with radiopaque filler, and the like. Likewise, in some embodiments, the inner and/or the outer layer, 34/30 or both, may be impregnated with, or be made of or include a material that may aid in MRI imaging. Some materials that exhibit these characteristics include, for example, tungsten, Elgiloy, MP35N, nitinol, and the like, and others. Those skilled in the art will recognize that these materials can vary widely without departing from the spirit of the invention.

Additionally, although depicted as including a generally round cross-sectional shape, it can be appreciated that the inner tubular member 24 can include other cross-sectional shapes or combinations of shapes without departing from the spirit of the invention. For example, the cross-sectional shape of the inner tubular member 24 may be oval, rectangular, square, triangular, polygonal, and the like, or any other suitable shape, depending upon the desired characteristics.

Referring to FIGS. 2 and 3, the reinforcing member 26 can also be a generally tubular member including a proximal region 36 having a proximal end 37 and a distal region 38 having a distal end 39. The reinforcing member 26 can be disposed about at least a portion of the inner tubular member 24 at a location along the length of the shaft 12 between proximal end 18 and distal end 22. In the embodiment shown, the reinforcing member 26 is disposed about the inner tubular member 26 along the proximal portion 16 of the shaft 12, but it should be understood that other locations are possible. The length of the reinforcing member 26 can also vary, depending upon, for example, the length of the shaft 12, the desired characteristics and functions of the catheter 10, and other such parameters. In some embodiments, the reinforcing member 26 has a length that allows it to be disposed over the majority of the length of the inner tubular member 24, and in some embodiments, is disposed about all but up to the distal most 15 cm or less of the inner tubular member 24. For example, the length of the inner tubular member 24 can be in the range of about 1-299 centimeters or more, or in some embodiments in the range of about 19 cm-249 cm.

Referring to FIG. 3, the reinforcing member 26 defines a lumen 40 that can be adapted and/or configured to house or surround a portion of the inner tubular member 24. In some embodiments, the reinforcing member 26 can have an inner diameter, defining the lumen 40, that is in the range of about 0.015 to about 0.06 inch in size, and in some embodiments, in the range of about 0.02 to about 0.035 inch in size. Additionally, in some embodiments, the reinforcing member 26 can have an outer diameter that is in the range of about 0.016 to about 0.07 in size, and in some embodiments, in the range of about 0.02 to about 0.04 inch in size. It should be understood however, that these, and other dimensions provided herein, are by way of example embodiments only, and that in other embodiments, the size of the inner and outer diameter of the reinforcing member 26 can vary greatly from the dimensions given, depending upon the desired characteristics and function of the device.

The reinforcing member 26 typically has an inner diameter that is greater than the outer diameter of the inner tubular member 24. As such, the reinforcing member 26 can be disposed about the inner tubular member 24 (i.e. a portion of the inner tubular member 24 is disposed within the lumen 40 of the reinforcing member) such that a space or gap 42 is defined between at least a portion of the outer surface 25 of the inner tubular member 24 and the inner surface 27 of the reinforcing member 26. In some embodiments, the space or gap 42 between at least a portion of the outer surface 25 of the inner tubular member 24 and the inner surface 27 of the reinforcing member 26 is in the range of about 0.0002 to about 0.004 inch in size, and in some embodiments, in the range of about 0.0005 to about 0.003 inch in size. It should be understood however, that these, and other dimensions provided herein, are by way of example embodiments only, and that in other embodiments, the size of the space or gap 42 can vary greatly from the dimensions given, depending upon the desired characteristics and function of the device.

Typically, the gap or space 42 remains open or unfilled by any other structure of the catheter along substantially the entire length of the reinforcing member 26, with the exception of small coupling points adjacent the proximal and distal ends 37/39 of the reinforcing member, for example, as will be set forth in more detail below. For example, in some embodiments, the gap or space 42 can extend between the outer surface 25 of the inner tubular member 24 and the inner surface 27 of the reinforcing member 26 along the length of the reinforcing member 26 in the range of about 50% or greater, 75% or greater, 90% or greater, or 95% or greater of the entire length of the reinforcing member 26. However, in other embodiments, other attachment points along the length of the reinforcing member 26 may be used, and as a result, multiple gaps or spaces may be created that may be separated by these additional attachment points, which may, in effect, fill portions of the gap 42. Still, such multiple gaps or spaces may still collectively extend along a substantial portion of the length of the reinforcing member, for example, in percentages of the total length as given above. As such, the reinforcing member 26 can act to reinforce or impart desired properties, such as tortional and lateral rigidity, to the catheter shaft 12, but allow at least the portion of the inner tubular member 24 surrounded by the gap or space 42 to move laterally within the lumen 40. Some examples of structure, methods, and techniques of coupling the reinforcing member 26 to the inner tubular member 24 will be discussed in more detail below.

The reinforcing member 26 can be adapted and/or configured to have a desired level of stiffness, torqueability, flexibility, and/or other characteristics. Those of skill in the art and others will recognize that the dimensions, structure, and materials of the reinforcing member 26 are dictated primarily by the desired characteristics, and the function of the final catheter 10, and that any of a broad range of the dimensions, structure, and materials can be used.

The desired stiffness, torquability, lateral flexibility, bendability or other such characteristics of the reinforcing member 26 can be imparted or enhanced by the structure of the reinforcing member 26. For example, the reinforcing member 26 may include a thin wall tubular structure, including one or a plurality of apertures 44, such as grooves, cuts, slits, slots, or the like, formed in a portion of, or along the entire length of, the tubular reinforcing member 26. Such structure may be desirable because it may allow reinforcing member 26, or portions thereof, to have a desired level of lateral flexibility as well as have the ability to transmit torque and pushing forces from the proximal region 36 to the distal region 38. The apertures 44 can be formed in essentially any known way. For example, apertures 44 can be formed by methods such as micro-machining, saw-cutting, laser cutting, grinding, milling, casting, molding, chemically etching or treating, or other known methods, and the like. In some such embodiments, the structure of the reinforcing member 26 is formed by cutting and/or removing portions of the tube to form apertures 44.

In some embodiments, the apertures 44 can completely penetrate the reinforcing member 26 such that there is fluid communication between the lumen 40 and the exterior of the reinforcing member 26 through the apertures 44. In some embodiments, the apertures 44 may only partially extend into the structure of the reinforcing member 26, either on the interior or exterior surface thereof. Some other embodiments may include combinations of both complete and partial apertures 44 through the structure of the reinforcing member 26. The shape and size of the apertures 44 can vary, for example, to achieve the desired characteristics. For example, the shape of apertures 44 can vary to include essentially any appropriate shape, such as squared, round, rectangular, pill-shaped, oval, polygonal, elongated, irregular, or the like, and may include rounded or squared edges, and can be variable in length and width, and the like.

Additionally, the spacing, arrangement, and/or orientation of the apertures 44, or in some embodiments, associated spines or beams that may be formed, can be varied to achieve the desired characteristics. For example, the number or density of the apertures 44 along the length of the reinforcing member 26 may vary, depending upon the desired characteristics. For example, the number or proximity of apertures 44 to one another near one end of the reinforcing member 26 may be high, while the number or proximity of slots to one another near the other end of the reinforcing member 26, may be relatively low, or vice versa. For example, in the embodiment shown in FIGS. 1 and 2, the distal region 38 of the reinforcing member 26 includes a plurality of apertures 44, while the proximal region 36 of the reinforcing member 26 does not include any apertures 44. As such, the distal region 38 can have a greater degree of lateral flexibility relative to the proximal region 36. In some embodiments, the distal about 10 to about 50% of the total length of the reinforcing member 26 can include apertures 44 defined therein, while the proximal about 50 to about 90% of the total length of the reinforcing member 26 is free of such apertures 44. For example, in some embodiments, the distal region 38 having a length in the range of about 30 to about 70 cm includes apertures 44 defined therein, while the remaining length in the proximal region 36 of the reinforcing member is free of such apertures 44. It should be understood however, that these, and other dimensions provided herein, are by way of example embodiments only, and that in other embodiments, the disposition of apertures 44 can vary greatly from the dimensions given, depending upon the desired characteristics and function of the device.

As suggested above, the apertures 44 may be formed such that one or more spines or beams 29 are formed in the tubular reinforcing member 26. Such spines or beams 29 (See FIGS. 2-6) could include portions of the tubular member 26 that remain after the apertures 44 are formed in the body of the tubular member. Such spines or beams 29 may act to maintain a relatively high degree of tortional stiffness, while maintaining a desired level of lateral flexibility. In some embodiments, some adjacent apertures 44 can be formed such that they include portions that overlap with each other about the circumference of the tube. In other embodiments, some adjacent apertures 44 can be disposed such that they do not necessarily overlap with each other, but are disposed in a pattern that provides the desired degree of lateral flexibility. Additionally, the apertures 44 can be arranged along the length of, or about the circumference of, the reinforcing member 26 to achieve desired properties. For example, the apertures 44 can be arranged in a symmetrical pattern, such as being disposed essentially equally on opposite sides about the circumference of the reinforcing member 26, or equally spaced along the length of the reinforcing member, or can be arranged in an increasing or decreasing density pattern, or can be arranged in a non-symmetric or irregular pattern.

Collectively, these figures and this description illustrate that changes in the arrangement, number, and configuration of slots may vary without departing from the scope of the invention. Some additional examples of arrangements of cuts or slots formed in a tubular body are disclosed in U.S. Pat. No. 6,428,489 and in Published U.S. patent application Ser. No. 09/746,738 (Pub. No. 2002/0013540), now U.S. Pat. No. 6,579,246, both of which are incorporated herein by reference. Also, some additional examples of arrangements of cuts or slots formed in a tubular body for use in a medical device are disclosed in U.S. patent application Ser. No. 10/375,493, now published as U.S. Patent Application Publication No. 2004/0167437, which is also incorporated herein by reference.

In addition to, or as an alternative to the structure of the reinforcing member 26, the materials selected for reinforcing member 26 may be chosen so that it has the desired characteristics. For example, reinforcing member 26 may be formed of materials having a desired modulus of elasticity. The reinforcing member 26 may be formed of any materials suitable for use, dependent upon the desired properties of the catheter 10. Some examples of suitable materials include metals, metal alloys, polymers, or the like, or combinations or mixtures thereof. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In some embodiments, it is desirable to use metals, or metal alloys that are suitable for metal joining techniques such as welding, soldering, brazing, crimping, friction fitting, adhesive bonding, etc. Additionally, in some embodiments, the reinforcing member 26 may be made of or include, be coated, plated, or clad with a radiopaque or MRI imaging material to facilitate radiographic visualization or MM imaging.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiment, the range of weight percent nickel and titanium, and or other trace elements may vary from these ranges. Within the family of commercially available nitinol alloys, are categories designated as "superelastic" (i.e. pseudoelastic) and "linear elastic" which, although similar in chemistry, exhibits distinct and useful mechanical properties.

In some embodiments, a superelastic alloy, for example a superelastic nitinol can be used to achieve desired properties. Such alloys typically display a substantial "superelastic plateau" or "flag region" in its stress/strain curve. Such alloys can be desirable in some embodiments because a suitable superelastic alloy will provide a reinforcing member 26 that is exhibits some enhanced ability, relative to some other non-superelastic materials, of substantially recovering its shape without significant plastic deformation, upon the application and release of stress, for example, during placement of the catheter in the body.

In some other embodiments, a linear elastic alloy, for example a linear elastic nitinol can be used to achieve desired properties. For example, in some embodiments, certain linear elastic nitinol alloys can be generated by the application of cold work, directional stress, and heat treatment, such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there is no martensite/austenite phase changes detectable by DSC and DMTA analysis in the range of about −60° C. to about 120° C. The mechanical bending properties of such material are therefore generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy allows the reinforcing member to exhibit superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

In some embodiments, the reinforcing member 26 can be formed of a shape-memory material, for example a shape memory alloy such as a shape memory nitinol. In such embodiments, the shape memory effect can be used in the deployment or use of the catheter, for example in causing the reinforcing member 26 to move from a first insertion configuration to a second use configuration, or, for example, for the reinforcing member 26 to "remember" its desired shape after deformation to another shape.

For example, in some embodiments, the reinforcing member 26 can include or be made of a shape memory alloy that is martensite at room temperature, and has a final austenite transition temperature ($A_f$) somewhere in the temperature range between room temperature and body temperature. For example, in some such embodiments, the shape memory alloy has a final austenite transition temperature in the range of about 25° C. and about 37° C. (e.g. body temperature). In some such embodiments, it may be desirable that the final austenite transition temperature be at least slightly below body temperature, to ensure final transition at body temperature. This feature allows the reinforcing member 26 to be inserted into the body of a patient in a martensitic state, and assume its preformed, austenitic shape when exposed to the higher body temperature within the anatomy, or at the target site. In this embodiment, deployment of the reinforcing member 26 can be achieved by a shape memory effect—as the material warms, it undergoes a transition from martensite to austenite form, causing transformation of the reinforcing member 26 from the first configuration to the second configuration.

In other example embodiments, the reinforcing member 26 can include or be made of a shape-memory alloy that could have a transition temperature $M_d$ (wherein $M_d$=highest temperature to strain-induced martensite) that is in the range of body temperature (e.g. 37° C.) or greater, below which the alloy retains sufficient stress-induced martensitic property to allow placement of the reinforcing member 26 at or above its final austenite transition temperature ($A_f$). In other words, this allows the catheter, including the reinforcing member 26 in its preformed austenitic state, to be inserted and navigated in the anatomy, where the reinforcing member may be exposed to stress that may promote portions thereof to undergo stress-induced martensitic (SIM) transformation. Thereafter, the reinforcing member 26 may recover its preformed, austenitic shape when released from the stress of navigation, at a temperature that may be substantially above the final austenite transition temperature without significant plastic, or otherwise permanent deformation. Additionally, in some such embodiments, the reinforcing member 26 can be constrained, for example, in a delivery device, such as a guide catheter, in a stress-induced martensitic (SIM) state, and recover its preformed, austenitic shape when released from the constraints of the catheter, at a temperature that may be substantially above the final austenite transition temperature without significant plastic, or otherwise permanent deformation. In these embodiments, the final austenite temperature may be quite low, e.g., 4° C. or lower, or it may be up to room temperature or higher.

In yet other embodiments, the reinforcing member 26 can include or be made of a shape memory alloy that is martensite at body temperature, and has a final austenite transition temperature ($A_f$) somewhere in the temperature range above body temperature. This feature allows the catheter including the reinforcing member 26 to be navigated in a martensitic state, and maintain a martensitic state until exposed to a temperature higher than body temperature. The reinforcing member 26 can then be heated to the necessary temperature above body temperature to make the transformation from martensite to austenite using an external heating means or mechanism. Such mechanisms may include the injection of heated fluid through the catheter, or other device, the use of electrical or other energy to heat the reinforcing member 26, or other such techniques. In some such embodiments, the shape memory alloy has a final austenite transition temperature in the range of about 37° C. to about 45° C. It may be desirable that the final austenite transition temperature be at least slightly above body temperature, to ensure there is not final transition at body temperature. Some examples of Nitinol cylindrical tubes having desired transition temperatures, as noted above, can be prepared according to known methods.

As noted above, the reinforcing member 26 may also be formed of or include polymer materials. Some examples of polymeric materials may include, but are not limited to: poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers, or mixtures or combinations thereof.

Referring now to FIG. 3, the distal portion 20 of the shaft 12 can include a distal region of the inner tubular member 24, and, in some embodiments, additional structure that can be adapted and/or configured to provide a distal tip structure 28 on the distal region of the catheter 10. For example, the distal tip structure 28 can be adapted and/or configured to provide characteristics such as shapability, flexability, steerability, atraumatic characteristics, and the like. For example, distal portion 20 including the inner tubular member 24, can also include one or more additional layers in addition to or disposed on the inner tubular member 24. Such additional layers may be made of any suitable material and by any suitable process, the materials and processes varying with the particular application and characteristics desired. For example, in the embodiment shown in FIG. 3, which is a partial cross-sectional view of a portion of the shaft 12, the distal portion 20 can include two additional layers 50 and 52 disposed about the inner tubular member 24. In the embodiment shown, an inner layer 50, which may be a reinforcement layer, such as a coil, braid, or the like, is disposed about the distal region of the inner tubular member 24, and an outer layer 52, such as a sleeve of material, for example, a polymer sleeve or layer, is disposed about the reinforcement layer 50 and the inner tubular member 24. It should be understood that in some embodiments it is not necessary that one or more of the layers include a reinforcing structure such as a coil or braid. It should also be understood that more or fewer layers can be used depending upon the desired characteristics of the device. Additionally, in some embodiments, a reinforcement layer 50 or structure, such as a coil or braid, may be embedded within a layer, or disposed between multiple layers.

Referring to FIG. 3, the reinforcement layer 50 illustrated can be a coil that has a generally circular cross-sectional shape, and is appropriately sized for disposal about the distal region of the shaft 12. A broad variety of other shapes and sizes could be used, for example, depending upon the size and shape of the distal region of the shaft. The coil 50 can be formed of a variety of materials including metals, metal alloys, polymers, and the like, for example, those materials discussed above with regard to the reinforcing member 26.

The coil 50 can be formed of round wire or flat ribbon ranging in dimensions to achieve the desired flexibility. In some embodiments, the coil 50 can be a round ribbon in the range of about 0.001-0.015 inches in diameter, and can have a length in the range of about 0.1 to about 20 cm; however, other dimensions and length are contemplated. The coil 50 can be wrapped in a helical fashion by conventional winding techniques. The pitch of adjacent turns of the coil 50 may be tightly wrapped so that each turn touches the succeeding turn or the pitch may be set such that the coil 50 is wrapped in an open fashion. Additionally, in some embodiments, the coil 50 or portions thereof can be made of or include or be coated, plated, or clad with a radiopaque or imaging material, as discussed above. Additionally, other radiopaque or MRI imaging structures can be incorporated into the structure of the distal portion 20, or other parts of the shaft 12. For example, a band, coil, ring, or other such structure made of or including radiopaque or MRI imaging material may be disposed about or within a portion of the shaft, for example, radiopaque or MRI ring 60. Such a structure can be incorporated within or disposed on the shaft using suitable techniques such as adhesive bonding, crimping, friction fitting, mechanically fitting, chemically bonding, thermally bonding, welding (e.g., resistance, Rf, or laser welding), soldering, brazing, or the use of a connector member or material, or the like, or combinations thereof.

The outer layer 52 can be a sheath or sleeve of material, such as a polymer material, disposed about the coil 50 and the inner tubular member 24. Some examples of suitable polymer materials include those listed above with regard to the inner tubular member, and the like. The outer layer 52 can be constructed and disposed using any appropriate technique, for example, by extrusion, co-extrusion, interrupted layer co-extrusion (ILC), coating, heat shrink techniques, heat bonding, casting, molding, fusing one or several segments of an outer layer material end-to-end, or the like. Securing the outer layer 52 to the coil 50 and/or the inner tubular member 24 may be achieved by the use of the above techniques, or in embodiments where the layer 52 is constructed independently of the other portions of the shaft 12, may be thereafter secured to the coil 50 and/or the inner tubular member 24 using suitable techniques such as adhesive bonding, crimping, friction fitting, mechanically fitting, chemically bonding, thermally bonding, welding (e.g., resistance, Rf, or laser welding), soldering, brazing, or the use of a connector member or material, or the like, or combinations thereof. Additionally, the outer layer 52 may be sized such that at least the portion thereof that is adjacent the reinforcing member has an outer diameter that is about the same as the outer diameter of the reinforcing member 26, so as to maintain a generally constant diameter in the transition between the reinforcing member 26 and the outer layer 52. Additionally, in some embodiments, the outer layer may include a portion that overlaps the distal end of the reinforcing member 26 to provide a smooth transition. In other embodiments, however, a tapered or step down transition may be provided. The distal portion 15 of the elongate shaft 12 may be curved as desired, or be adapted and/or configured to be curved as desired, depending on the particular application.

Now some example embodiments of structure, methods, and techniques of coupling structure of the catheter 10, such as the manifold 14, reinforcing member 26, and distal tip structure 28 to the inner tubular member 24, will be discussed in more detail.

Refer now to FIG. 3, which illustrates one example embodiment of a portion of a catheter shaft 12, including the inner tubular member 24, the reinforcing member 26, and the distal tip structure 28 as discussed above. The distal region 36 of the reinforcing member 26 can be connected to the inner tubular member 24 using suitable techniques such as adhesive bonding, friction fitting, mechanically fitting, crimping, chemically bonding, thermally bonding, welding (e.g., resistance, Rf, or laser welding), soldering, brazing, or the use of a connector member or material, or the like, or combinations thereof. In the embodiment shown, the distal end 39 of the reinforcing member 26 can be connected to the inner tubular member 24 using an adhesive material 62, for example, a cyanoacrylate, or other suitable type of adhesive. In at least some embodiments, only a relatively small portion of the distal region 38 adjacent the distal end 39 of the reinforcing member 26 is connected to the inner tubular member 24. For example, the adhesive or other material or structure used to make the connection may only extend under or within five or fewer of the apertures 44, or in some embodiments, as shown in FIG. 3, three or even two or fewer of the apertures 44. The coil 50 can be slid onto the distal region 38 of the inner tubular member 24, such that it is in line with or butts up to the reinforcing member 26, and can be connected to the inner tubular member 24 using suitable techniques, such as those described above. In some embodiments, the reinforcing member and the coil 50 can be connected to the inner tubular member 24 at the same time and/or using the same attachment material, such as an adhesive. In other embodiments, they may be attached separately and/or using separate attachment techniques. Any radiopaque or Mill structures, such as the ring 60, can be attached to the coil 50, using suitable attachment techniques, as discussed above. For example, the ring 60 may be attached to the coil 50 by crimping the ring to the coil adjacent the distal end 39 of the reinforcing member 26. In such a configuration, the placement of the ring 60 may also aid in providing a more gradual transition or step down in diameter from the reinforcing member 26 to the coil 50. The outer layer 52, such as a polymer material, can be disposed about the ring 60, the coil 50 and the inner tubular member 24. As discussed above, the outer layer 52 may be sized appropriately so as to maintain a generally constant diameter in the transition between the reinforcing member 26 and the outer layer 52, and may include portion 65 that overlaps the distal end of the reinforcing member 26 to provide a smooth transition.

Figure 4:
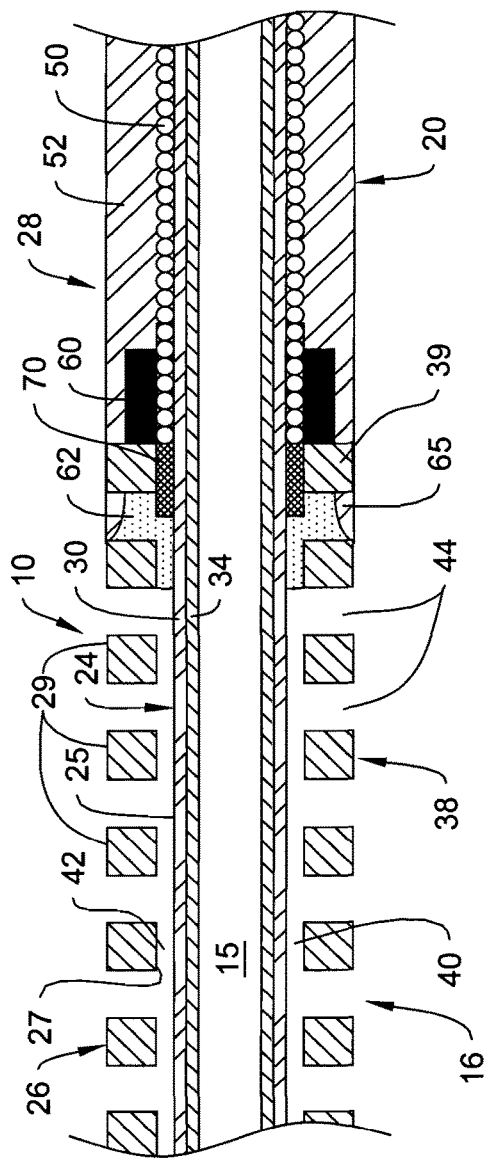
FIG. 4 is a partial cross sectional view similar to the view of FIG. 3, but of another example embodiment of a medical device.

Refer now to FIG. 4, which shows an alternative construction similar to that shown in FIG. 3, wherein similar elements are numbered the same. In FIG. 4, however, a ring 70 of material, such as polymer material, heat shrink material, or the like, is disposed about the inner tubular member 24 under the distal end 39 of the reinforcing member 26. In such embodiments, the use of the ring 70 disposed between the inner tubular member 24 and the reinforcing member 26 can aid in maintaining the bonding and integrity of the joint or connection.

Refer now to FIG. 5, which shows another alternative construction similar to that shown in FIG. 3, wherein similar elements are numbered the same. In FIG. 5, however, the ring 60 is absent. Additionally, in this embodiment, the coil 50 extends proximally such that a proximal portion of the coil 50 is disposed about the inner tubular member 24 under the distal end 39 of the reinforcing member 26. In such embodiments, the placement of a proximal portion of the coil 50 between the inner tubular member 24 and the reinforcing member 26 can aid in maintaining the bonding and integrity of the joint or connection. This embodiment also shows a continuous layer of adhesive material 62 that is used to connect the reinforcing member 26 and the coil 50 to the inner tubular member 24. The outer layer 52 can be disposed about the coil 50, the adhesive material 62, and the inner tubular member 24, and may also include a portion 65 that overlaps the distal end of the reinforcing member 26 to provide a smooth transition.

Refer now to FIG. 6, which shows another alternative construction similar to that shown in FIG. 3, wherein similar elements are numbered the same. In FIG. 6, however, the ring 60 is absent. Additionally, this embodiment shows a continuous layer of adhesive material 62 that is used to connect the reinforcing member 26 and the coil 50 to the inner tubular member 24, and also includes an outer layer 52 that includes a cutout or stepped up portion 80 that can accommodate a greater amount of adhesive material. In some embodiments, the adhesive material may also act to connect the outer layer 52 to the shaft 12.

Referring back to FIGS. 1 and 2, at the proximal end of the shaft 12, the manifold 14 may be secured to the inner tubular member 24 and/or the reinforcing member 26 at the proximal end 18 of the shaft 12 using any suitable technique, for example, by adhesive, friction fitting, mechanically fitting, chemically bonding, thermally bonding, heat shrink materials, molding, casting, welding (e.g., resistance or laser welding), soldering, brazing, the use of an outer sleeve or polymer layer to bond or connect the components, or the like, or combinations thereof. In some embodiments, the distal end of the manifold 14 can be cast, molded or shaped onto the proximal end 18 of the shaft 12 such that it is connected to the proximal end 18, and can also act as a connector between the inner tubular member 24 and/or the reinforcing member 26. For example, the manifold may be made of a polymeric material, such as a polycarbonate material, or the like, that could be molded or cast onto the proximal end 18 of the shaft 12. For example, refer now to FIG. 7, which shows the manifold 14 attached to the proximal end 18 of the shaft 12. The manifold 14 can be cast, molded or shaped onto the proximal end 18 of the shaft 12 such that it can include a protrusion 91 that extends between and interconnects the inner tubular member 24 and the reinforcing member 26, and may also include an overlapping portion 93 that may help to maintain connection, and may provide a smooth transition between the manifold 14 and the reinforcement member 26.

A lubricious, a hydrophilic, a protective, or other type of coating may be applied over portions or all of the shaft 12. Hydrophobic coatings such as fluoropolymers provide a dry lubricity which improves catheter handling and device exchanges. Lubricious coatings can aid in insertion and steerability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It should also be understood that in some embodiments, a degree of MM compatibility can be imparted into catheter 10. For example, to enhance compatibility with Magnetic Resonance Imaging (MRI) machines, it may be desirable to construct portions of the reinforcing member 26, the coil 50, or other portions of the catheter 10, in a manner, or use materials that would impart, a degree of MRI compatibility. For example, the lengths of relatively conductive structures within the catheter 10 may be limited to lengths that would not generate undue heat due to resonance waves created in such structures when under the influence of an MRI field generated by an MRI machine. Alternatively, or additionally, portions, or all of the catheter may be made of a material that does not substantially distort the image and create substantial artifacts (artifacts are gaps in the image). Certain ferromagnetic materials, for example, may not be suitable because they may create artifacts in an MRI image. Additionally, all or portions of the catheter may also be made from a material that the MRI machine can image, as described above. Some materials that exhibit these characteristics include, for example, tungsten, Elgiloy, MP35N, nitinol, and the like, and others.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What is claimed is:

1. A medical device, comprising:
   a tubular member having a plurality of slots formed therein;
   a tubular liner disposed along an inner surface of the tubular member, the tubular liner including a tip region that extends distally beyond a distal end of the tubular member and a proximal end that is radially spaced from a proximal end of the tubular member;
   a tip member coupled to the tip region; and
   a hub coupled to the proximal end of the tubular member and coupled to the proximal end of the tubular liner, wherein at least a portion of the hub extends along an inner surface of the tubular member; and
   wherein the hub is attached to an outer surface of the tubular member.

2. The medical device of claim 1, wherein the portion of the hub extending along the inner surface of the tubular member defines a hub projection that extends between the proximal end of the tubular member and the proximal end of the tubular liner.

3. The medical device of claim 1, wherein the tubular member includes a super elastic nickel-titanium alloy.

4. The medical device of claim 1, wherein the tubular member includes a linear elastic nickel-titanium alloy.

5. The medical device of claim 1, wherein the tip member includes a radiopaque marker.

6. The medical device of claim 1, wherein the tip member includes a coil.

7. The medical device of claim 1, wherein the tubular liner includes two or more layers.

8. The medical device of claim 1, wherein at least a portion of the tubular liner is movable relative to the tubular member.

9. The medical device of claim 1, wherein the hub includes an adapter for attaching a secondary medical device to the hub.

10. A medical device, comprising:
    a hub having a distal end region and a proximal end region, the proximal end region including an adapter;
    an elongate shaft coupled to the distal end region of the hub, the elongate shaft having a plurality of cuts formed therein;
    a tubular liner disposed within the shaft, the tubular liner including a tip region that extends distally beyond a distal end of the shaft and a proximal end;
    wherein the proximal end of the tubular liner and a proximal end of the shaft are radially spaced and axially aligned; and
    wherein the hub includes a hub projection that extends between the proximal end of the tubular liner and the proximal end of the shaft.

11. The medical device of claim 10, wherein a tip member is coupled to the tip region of the tubular liner.

12. The medical device of claim 11, wherein the tip member includes a radiopaque marker.

13. The medical device of claim 11, wherein the tip member includes a coil.

14. The medical device of claim 10, wherein the tubular liner includes two or more layers.

15. The medical device of claim 10, wherein at least a portion of the tubular liner is movable relative to the shaft.

16. A medical device, comprising:
    a hub having a distal attachment region and a proximal adapter;
    an elongate shaft coupled to a first attachment portion of the distal attachment region;
    wherein the shaft includes a distal end and a plurality of cuts;
    a tubular liner disposed within the shaft and coupled to a second attachment portion of the distal attachment region;
    wherein the tubular liner extends through the shaft and includes a tip section extending distally of the distal end of the shaft;
    a tip member coupled to the tip section of the tubular liner;
    wherein the first attachment portion is radially spaced from the second attachment portion such that a gap is defined between the shaft and the tubular liner; and
    wherein the hub includes a hub projection that extends into the gap.

17. The medical device of claim 16, wherein the tubular liner includes two or more layers.

18. The medical device of claim 16, wherein at least a portion of the tubular liner is movable relative to the shaft.

* * * * *